United States Patent [19]
Borzeix

[11] Patent Number: 6,057,302
[45] Date of Patent: May 2, 2000

[54] SOPHOROLIPIDS AS STIMULATING AGENT OF DERMAL FIBROBLAST METABOLISM

[75] Inventor: Frédérique Borzeix, Rueil Malmaison, France

[73] Assignees: Institut Francais du Petrole; Sophor S.A., both of France

[21] Appl. No.: 08/889,367

[22] Filed: Jul. 8, 1997

[30] Foreign Application Priority Data

Dec. 27, 1996 [FR] France .................................. 96 16093

[51] Int. Cl.$^7$ .................................................. A61K 31/739
[52] U.S. Cl. .................................. 514/54; 514/25; 514/53
[58] Field of Search ................................ 514/25, 53, 54

[56] References Cited

U.S. PATENT DOCUMENTS 5,756,471  5/1998  Hillion et al. .......................... 514/25

FOREIGN PATENT DOCUMENTS 0 209 783  1/1987  European Pat. Off. .
95/34282  12/1995  WIPO .

OTHER PUBLICATIONS

Database WPI, Section Ch, Week 8008 (AN 80–13763C), Derwent Publications Ltd., London, GB. JP 55004344A, Jan. 12, 1980.

*Primary Examiner*—Kathleen K. Fonda
*Attorney, Agent, or Firm*—Millen, White, Zelano & Branigan, P.C.

[57] ABSTRACT

The use of at least one sophorolipid in cosmetics as an agent for stimulating the metabolism of fibroblasts of the dermis of the skin, particularly as an agent that restructures the skin, agent that repairs the skin, and/or an agent that tones up the skin.

32 Claims, No Drawings

SOPHOROLIPIDS AS STIMULATING AGENT OF DERMAL FIBROBLAST METABOLISM

The invention relates to the use of at least one sophorolipid as an agent for stimulating the metabolism of the fibroblast cells of the dermis of the skin. It pertains particularly to the fields of cosmetology and dermatology.

The properties of sophorolipids that relate to combatting skin ageing, namely their antiradical and anti-elastic action, were described in Patent Application WO95/34282. In no case have the properties that relate to the stimulation of the metabolism of the fibroblasts that it is proposed to develop here been described or suggested.

The mechanical properties of the skin are, for the most part, ensured by the collagen fibers that constitute the main structure of the matrix of the dermis.

The collagens constitute a family of about twenty separate proteins, half of which are represented in the dermis. These are proteins that are rich in prolines and hydroxyprolines, synthesized by the fibroblasts.

During ageing, the metabolism and/or the structure of the collagens can be modified. A reduction of the synthesis of collagens and an increase in the crosslinking of the fibers are observed. Furthermore, during skin ageing, cellular renewal is slowed down.

Products of animal origin, such as embryo extracts, the extracts of mammary glands, placental extracts, and amniotic fluid, have been widely used in personal care products for their properties of stimulating cellular activity and therefore their preventative action against skin ageing.

Owing to the appearance in 1986 of mad cow disease, these raw materials are no longer used in the cosmetics industry.

Thus, products such as oligoelements like zinc, copper, and manganese can stimulate fibroblast proliferation and increase in particular the production of collagen by the fibroblasts.

In contrast, ascorbic acid (vitamin C) makes it possible to increase the synthesis of collagens. It should be noted that the brittleness of vitamins makes it difficult to incorporate them as is into the finished products. Furthermore, their shelf life and resistance to heat, pH, or light are limited.

Consequently, the use of natural products of vegetable origin that do not have the problem of stability and which, moreover, are easy to incorporate into a formulation is being sought at this time in the fields of cosmetology and dermocosmetology. This is one of the objects of the invention.

In this connection, the sophorolipids, glycolipids of natural origin, that are obtained by yeast fermentation meet the expected needs. Actually, in vitro studies have shown that sophorolipids have a beneficial effect on the synthesis of collagens by the dermal fibroblasts and are good agents for stimulating cellular division.

Their effectiveness, compared to that of fetal calf serum and vitamin C, has been demonstrated in vivo. Their action as agents for restructuring and repairing tissue makes them active products for combatting skin ageing. More specifically, sophorolipids stimulate the synthesis of collagen in vitro, which makes it possible for cosmetological applications to use them as agents that restructure the skin.

Sophorolipids stimulate significantly the cells of the human skin and thereby promote the reconstruction of connective tissue. It is therefore possible to use them as agents for repairing the skin. Finally, increasing the adhesion of the fibroblast cells to the culture substrates in the presence of sophorolipids makes it possible to justify their use as agents that tone up the skin (skin firmness). Quite obviously, they can exhibit all of these properties.

All of these properties ensure that sophorolipids, by promoting the reconstruction of connective tissue, can have a repairing action as well as a preventative action against skin ageing.

Sophorolipids in acid form can be used in concentration ranges that vary from 30 ppm to 10% by weight to volume (p/v) of active ingredients of formulation and particularly in emulsions of the water/oil and oil/water type (milks, creams) or in gels and serums. They will be used more particularly in concentration ranges that vary from 0.02% to 1% of active ingredient. The sophorolipids in raw form can be used at concentrations that range from 30 ppm to 6% of active ingredient and more particularly from 80 ppm to 2%.

The sophorolipids in raw form are obtained by fermentation according to the process that is described in Patent FR 2670 798 that is cited in reference and that relates to the production of sophorolipids by fermentation with continuous supply (Fed batch) of fatty acid esters or oil.

The sophorolipids in deacetylated acid form are obtained after alkaline hydrolysis of the sophorolipids in raw form and neutralization (Davila et al., 1993—Journal of Chromatography 648, 139–149).

The residual acetic acid that is contained in the hydrolysis product is eliminated by a standard separation method, i.e., by running the material over an anionic resin of type IRA 93.

Sophorolipids are glycolipids of vegetable origin that are perfectly biodegradable. Their structure consists of a glucidic fraction that is represented by a dimer of glucose, sophorose (2-O-β-D-glucopyranosyl, β-D-glucopyranose) connected by an acetal bond to a fatty hydroxyacid in terminal or subterminal position.

The fatty hydroxyacids that are most represented comprise 16 to 18 carbon atoms and can be mono-saturated or di-unsaturated. The fatty hydroxyacid that is most incorporated into the sophorolipids, regardless of the lipidic substrate that is used, is 17-hydroxyoleic acid (Table 1).

The sophorolipids consist of a mixture of glycolipids of related structures that are distinguished from one another by lactonization or non-lactonization of sophorose (mainly in 4"-position) or else by the degree of acetylation of the latter.

The form that is represented most strongly ($\geq 80\%$) in the sophorolipids in raw form is the lactonic form.

TABLE 1

Distribution of the constituent fatty hydroxyacids of the sophorolipids that are obtained by fermentation from glucose and colza oil ester

| Fatty Acids | % |
| --- | --- |
| 15-OH C16:0 | 1.7 |
| 16-OH C16:0 | 1.2 |
| 17-OH C18:2 | 6.7 |
| 17-OH C18:1 | 63.4 |
| 17-OH C18:0 | 3.2 |
| 18-OH C18:2 | 13.5 |
| 18-OH C18:1 | 1.03 |

The following examples illustrate the invention.

EXAMPLE 1

Effect of Sophorolipids in Acid Form on the Neosynthesis of Collagens

In vitro study in a monolayer system.

The focus here is on the effect of sophorolipids in acid form on one of the stages of the metabolism of collagens, that of neosynthesis.

An in vitro model that is based on the use of human dermis fibroblasts that are cultivated in collagen lattices (equivalent dermis) was adopted for evaluating the effects of sophorolipids in acid form.

The collagen molecules contain a large proportion of proline; therefore the incorporation of proline into the proteins, basically into the collagens, was measured.

The specifications of the sophorolipids in acid form are given below:

| dry material | ≦25% ± 2% |
|---|---|
| pH | 6 ± 0.5 |
| minerals | ≦1% |
| free sugars | ≦1% |
| free fatty acids | ≦0.5% |
| acetate | ≦1%. |

The reference products for carrying out the tests are:
sodium ascorbate (vitamin C)
fetal calf serum (SVT)

The fibroblast cells that are obtained from dermis explants were cultivated and used in the seventh pass.

The test systems consist of collagen lattices that are contracted by the fibroblasts after 96 hours of cultivation.

The sophorolipids in acid form as well as the reference molecules are immediately dissolved in the incubation medium and then brought together with the test systems to which incubation medium that contains tritiated proline has been added.

The lattices are then incubated for 72 hours at 37° C., under an atmosphere that contains 5% $CO_2$.

The measurement of the incorporation of the tritiated proline is done as follows:

The lattices were incubated for one hour, while being stirred gently and at ambient temperature. The samples were then placed in scintillation flasks. Radioactivity was measured with a PACKARD counter. The values were expressed in cpm per lattice.

Test cultures (without a product under test) were carried out concurrently. Each experimental condition was run in triplicate.

The data groups (test group and treated groups) were studied by one-factor analysis of variance (ANOVA 1), followed by a Dunnett test (p=probability of being outside the margin of error).

The effects of sophorolipids in acid form on the synthesis of collagens were studied in an equivalent dermis model. The latter consisted of collagen lattices contracted by dermal fibroblasts of a 23-year-old woman.

Vitamin C and fetal calf serum were used as reference products. The product under test and the reference products were diluted in the incubation medium and incubated the equivalent dermis for 72 hours.

The effects on the synthesis of the collagens were evaluated by measuring the incorporation of $^3H$-proline into the proteins that are neosynthesized by the fibroblasts. In the model used, the incorporation of the tritiated proline into the proteins took place mainly in the collagens.

An evaluation of the effects of sophorolipids in acid form and reference products on the neosynthesis of collagens shows that:
  the fetal calf serum at 10% (v/v) increases by a factor of 4.1 the synthesis of collagens (Table 2).
  vitamin C at 1 mg/ml increases by a factor of 1.8 the incorporation of proline that is tritiated in the neosynthesized proteins (Table 2).
  sophorolipids in acid form that are tested at 0.2:1 and 5 mg/ml significantly increase the incorporation of tritiated proline into the neosynthesized proteins by a factor of 2; 1.5 and 1.6, respectively (p<0.05) (Table 3).

The sophorolipids in acid form stimulate the synthesis of collagen in this equivalent dermis model and manifest an effect that restructures the skin.

TABLE 2

Effect of fetal calf serum (SVF) and vitamin C on the incorporation of tritiated proline into the collagens that are neosynthesized by fibroblasts, in an equivalent dermis model

|  | Control | SVF 10% (v/v) | Vitamin C 1 mg/ml |
|---|---|---|---|
| cpm/lattice | 52 | 235 | 97 |
|  | 54 | 201 | 95 |
|  | 47 | 193 | 89 |
| mean ± standard deviation | 51 ± 4 | 210* ± 22 | 94* ± 4 |
| % relative to the control | 100 | 411 | 184 |

*: the mean of the group is significantly different from the mean of the control group (p < 0.05)

TABLE 3

Effect of sophorolipids in acid form in the incorporation of tritiated proline into the collagens neosynthesized by fibroblasts, in an equivalent dermis model

|  | Concentration (mg/ml) | | | |
|---|---|---|---|---|
|  | 0 | 0.2 | 1 | 5 |
| cpm/lattice | 52 | 104 | 91 | 87 |
|  | 54 | 132 | 88 | 83 |
|  | 47 | 87 | 54 | 76 |
| mean ± standard deviation | 51 ± 4 | 108* ± 23 | 78 ± 21 | 82* ± 6 |
| % relative to the control | 100 | 211 | 152 | 161 |

*: the mean of the group is significantly different from the mean of the control group (p < 0.05)

EXAMPLE 2

Effect of Sophorolipids in Raw Form on the Synthesis of Collagens

Monolayer model: human dermal fibroblasts that are cultivated in lattices

The experimental implementation is similar to that described in Example 1. The study was made here on sophorolipids in raw form.

The specifications of the sophorolipids in raw form are provided below:

| dry material | ≦30% ± 2% |
|---|---|
| pH | 7 ± 0.5 |
| minerals | ≦2% |
| free sugars | ≦1% |
| free fatty acids | ≦3% |
| ashes | ≦0.04% |
| density | 1.03 at 20° C. |
| viscosity | 115.3 mpa · s at 20° C. |
|  | 62.4 mpa · s at 40° C. |

Evaluation of the effects of sophorolipids in raw form on synthesis of the collagens in an equivalent dermis model shows that:
  the sophorolipids in raw form are tested at 0.08 µg/ml; 0.4 µg/ml and 2 µg/ml significantly increase the incorporation of tritiated proline into the neosynthesized proteins by a factor of 2.3, 2.2, and 2, respectively (p<0.05) (Table 4). These results do not show the dose effect of the product under test, with the maximum stimulation being obtained from the concentration that is equal to 0.08 µg/ml.

Sophorolipids in raw form therefore stimulate the synthesis of collagen in this equivalent dermis model and exhibit a skin restructuring effect.

TABLE 4

Effect of sophorolipids in raw form, fetal calf serum, and vitamin C on the incorporation of tritiated proline into collagens neosynthesized by fibroblasts, in an equivalent dermis model

|  | Concentration (µg/ml) | | | SVF | Vitamin C 1 |
| --- | --- | --- | --- | --- | --- |
|  | 0 | 0.08 | 0.4 | 2 | (v/v) | mg/ml |
| cpm/ lattice | 52 54 47 | 116 116 120 | 110 95 131 | 94 96 122 | 235 201 193 | 97 95 89 |
| mean ± standard deviation | 51 ± 4 | 117* ± 2 | 112* ± 18 | 104* ± 16 | 210* ± 22 | 94* ± 4 |
| % relative to the control | 100 | 230 | 220 | 204 | 411 | 184 |

*: The mean of the group is significantly different from the mean of the control group (p < 0.05).

EXAMPLE 3

Effect of Sophorolipids in Acid Form on the Synthesis of Collagens and Cellular Division In vitro study in a reconstructed skin model.

The focus here is on an experimental SKIN$^2$ model that corresponds to reconstructed skin with an epidermis and a dermis.

To evaluate the effect of sophorolipids in acid form on the synthesis of collagens, the incorporation of tritiated proline into the acid-soluble proteins was measured. In contrast, the viability of the SKIN$^2$ skins was measured at the end of the treatment.

The sophorolipids in acid form, whose specifications were described in Example 1, were tested at 1 and 10 mg/ml.

The mixture that consists of 0.2 mg/ml of vitamin C and 10% (v/v) of SVF was used as a positive reference.

The reconstituted SKIN$^2$ skins were used according to the manufacturer's instructions.

The products, which were immediately dissolved in the test medium, were applied to the epidermis one hour per day for three consecutive days.

The effects on the synthesis of the collagen were evaluated by measuring the incorporation of $^3$H-proline into the proteins that are neosynthesized by the fibroblasts. This incorporation took place mainly in the collagen molecules.

The viability of the SKIN$^2$ skins was checked by the colorimetric technique with MTT (dimethyl-thiazole diphenyl tetrazolium bromide).

The results show that the vitamin C+SVF mixture is not cytotoxic (Table 5) and that it increases by a factor of 1.3 the incorporation of tritiated proline into the neosynthesized proteins (Table 5).

The sophorolipids in acid form that are tested at 1 and 10 mg/ml are not cytotoxic compared to SKIN$^2$ skins (Table 5).

At 1 and 10 mg/ml, they increase by factors of 1.4 and 1.2, respectively the reduction of MTT by the cells. This can correspond to an increase of cellular metabolism at an equal number of cells, or an increase of the number of cells, i.e., stimulation of cellular division.

At 10 mg/ml, they increase by 14% the incorporation of tritiated proline into the neosynthesized proteins (Table 6).

The lower amplitude of increase observed in this work compared to the results that are obtained in the monolayer model can be explained by a lower response capacity in the SKIN$^2$ model relative to the fibroblasts in a monolayer: the stimulation factor that is obtained with SVF was 1.3 in the SKIN$^2$ model versus 4 in the monolayer model (Example 1).

Cellular metabolism is different in the two cultivation methods: in the SKIN$^2$ model, the fibroblasts are capable of division, which is not the case in a monolayer, and it is well known that the division-phase cells are less differentiated and synthesize fewer proteins of the extracellular matrix.

These elements can explain the fact that the stimulation potential of the sophorolipids is reflected differently in the two situations: by an increase of cellular metabolism and/or the number of cells in SKIN$^2$ and by an increase of the neosynthesis of proteins in a monolayer. In the skin in the normal state, the fibroblasts are confluent, and it is rather the "collagen" parameter that would be influenced, whereas in skin that is being restructured (in a state of scarring, for example), it is rather the "division" parameter that would be increased.

In any case, the sophorolipids in acid form, in the two studies made, prove to be a significant stimulant of the cells of the human skin, in low concentration ranges.

TABLE 5

Effect of sophorolipids in acid form and the reference product, vitamin C + SVF, on the viability of reconstructed SKIN$^2$ skins. Measurement of the reduction of MTT

|  | Control | Sophorolipids in acid form (mg/ml) | | Reference product |
| --- | --- | --- | --- | --- |
|  |  | 1 | 10 |  |
| mU DO/sample | 215 224 234 | 356 293 277 | 226 278 374 | 230 138 170 |
| mean ± standard deviation | 224 ± 10 | 309$^\#$ ± 42 | 276$^\#$ ± 49 | 179 ± 47 |
| % relative to the control | 100 | 138 | 123 | 80 |

$^\#$: Mean significantly different from the control group, p < 0.08

TABLE 6

Effect of sophorolipids in acid form and the reference product, vitamin C + SVF, on the synthesis of collagens in reconstructed SKIN$^2$ skins. Evaluation by measuring the incorporation of proline H$^3$ into the acid-soluble proteins

|  | Control | Sophorolipids in acid form (mg/ml) | | Reference product |
| --- | --- | --- | --- | --- |
|  |  | 1 | 10 |  |
| cpm/ sample | 14281 15526 | 15788 14960 | 17822 16220 | 18732 18235 |

TABLE 6-continued

Effect of sophorolipids in acid form and the reference product, vitamin C + SVF, on the synthesis of collagens in reconstructed SKIN² skins. Evaluation by measuring the incorporation of proline H³ into the acid-soluble proteins

|  | Control | Sophorolipids in acid form (mg/ml) 1 | Sophorolipids in acid form (mg/ml) 10 | Reference product |
|---|---|---|---|---|
|  | 14665 | 15594 | 16845 | 19102 |
| mean ± standard deviation | 14824 ± 638 | 15447 ± 433 | 16962# ± 807 | 18690* ± 435 |
| % relative to the control | 100 | 104 | 114 | 126 |

: Mean significantly different from the control group, p < 0.08
*: mean significantly different from the control group, p < 0.05

EXAMPLE 4

Effect of Sophorolipids in Raw Form on the Synthesis of Collagens and cellular Division—Reconstructed SKIN² Skin Model The focus here is on the effects of sophorolipids in raw form on the synthesis of collagens and on cellular division in a reconstructed skin model.

The experimental conditions are identical to those that are described in Example 3. The specifications of the sophorolipids in raw form that are used are those that are described in Example 2.

The results showed that the sophorolipids in raw form at 0.1, 1, 10, and 100 µg/ml were not cytotoxic compared to SKIN² skins (Table 7). At 0.1 µg/ml, they increase by a factor of 1.6 the reduction of MTT by the cells. This may correspond to an increase in cellular metabolism at an equal number of cells or to an increase in the number of cells, i.e., a stimulation of cellular division. The sophorolipids in raw form at 1 and at 10 µg/ml increase by 10% the incorporation of tritiated proline (Table 8).

As in the case of sophorolipids in acid form, it seems that the stimulation potential of the sophorolipids in raw form manifests itself differently in the two situations: by an increase in cellular metabolism and/or the number of cells in SKIN² and by an increase in the neosynthesis of proteins in a monolayer (Example 2). In skin in the normal state, the fibroblasts are confluent, and on the whole the "collagen" parameter would be influenced, whereas in a skin which is being restructured (in a scarring state, for example), on the whole the "division" parameter would be increased.

In any case, the sophorolipids in raw form, in the two studies made, prove to be significant stimulants of the cells of the human skin in low concentration ranges.

TABLE 7

Effect of sophorolipids in raw form and the reference product, vitamin C + SVF, on the viability of the reconstructed SKIN² skins -- measurement of the reduction of the MTT

|  | Control | Reference product | Concentration (µg/ml) of sophorolipids in raw form 0.1 | 1 | 10 | 100 |
|---|---|---|---|---|---|---|
| mU DO/ sample | 215 | 230 | 349 | 146 | 199 | 174 |
|  | 224 | 138 | 319 | 201 | 242 | 169 |
|  | 234 | 170 | 377 | 168 | 148 | 176 |
| mean ± standard deviation | 224 ± 10 | 179 ± 47 | 348# ± 29 | 172 ± 28 | 196 ± 47 | 173 ± 4 |
| % relative to the control | 100 | 80 | 155 | 77 | 88 | 77 |

: mean significantly different from the control group, p < 0.08

TABLE 8

Effect of sophorolipids in raw form and the reference product, vitamin C + SVF, on the synthesis of collagens in the reconstructed SKIN² skins. Evaluation by measuring the incorporation of proline H³ into the acid-soluble proteins

|  | Control | Reference product | Concentration (µg/ml) of sophorolipids in raw form 0.1 | 1 | 10 | 100 |
|---|---|---|---|---|---|---|
| cpm/ sample | 14281 | 18732 | 17225 | 18143 | 17753 | 15326 |
|  | 15526 | 18235 | 14332 | 16315 | 16518 | 17124 |
|  | 14665 | 19102 | 14576 | 13827 | 14642 | 12963 |
| mean ± standard deviation | 14824 ± 638 | 18690* ± 435 | 15378 ± 1604 | 16095 ± 2166 | 16304 ± 1566 | 15138 ± 2087 |
| % relative to the control | 100 | 126 | 104 | 109 | 110 | 102 |

*mean significantly different from the control group, p < 0.05

EXAMPLE 5

Effect of Sophorolipids in Acid Form on the Adhesion Properties of Human Dermal Fibroblasts It is proposed to evaluate the properties of the sophorolipids in acid form compared to relations between the fibroblasts of the skin dermis and their environment. More specifically, the effects of the product on the adhesion of fibroblasts to a culture surface that may or may not be covered by collagen were measured.

The fibroblasts obtained by culturing skin explants were used on the twelfth pass. Microtitration plates of 24 untreated culture wells were used for the tests, with or without a collagen cover.

The sophorolipids in acid form, tested at 0.2; 1 and 5 mg/ml, as well as the fetal calf serum, tested at 2% and 10% (v/v), are diluted in the medium that contains fibroblasts at a level of 75,000 cells per well and incubated at 37° C. The number of adhesive cells in the culture wells was evaluated by the reduction method of the MTT (measurement of cell viability).

The effects of the sophorolipids in acid form on the adhesion of the human dermal fibroblasts to a plastic surface that may or may not be covered by collagen were evaluated. Fetal calf serum was used as a reference product.

The results show that:

a) On a plastic hydrophobic substrate, not treated for the cultivation of cells and not covered by collagen
   in the presence of SVF at 2% (v/v), the number of adhesive cells was comparable to the control after 25 minutes of incubation. The SVF at 10% (v/v) increased by a factor of 1.2 the number of adhesive cells (Table 9). This effect validated the tests.
   the sophorolipids tested at 0.2 mg/ml increased by a factor of 1.5 the number of adhesive cells. At 1 and 5 mg/ml, the adhesion of the cells to the substrate was comparable to that of the control (Table 9).

b) On a culture substrate that was not treated for the cultivation of cells and was covered with collagen
   in the presence of SVF at 2 and 10% (v/v), the number of adhesive cells was comparable to the control after 25 minutes of incubation (Table 10). This effect validated the test.
   the sophorolipids tested at 0.2 mg/ml increased by a factor of 1.4 the number of adhesive cells. At 1 mg/ml and 5 mg/ml, the adhesion of the cells to the substrate was comparable to that of the control (Table 10).

In conclusion, in this in vitro study, the sophorolipids in acid form increase the adhesion of the fibroblasts to the culture substrate. These results may indicate a modification by the sophorolipids of the cellular membrane or components of the latter and modulation of the relations of the dermal fibroblasts with the matrix environment in particular. These data make it possible to claim that the sophorolipids in acid form contribute to skin firmness. Generally, it appears that the acid form proves particularly advantageous because of a lower cytotoxicity than that of the raw form.

TABLE 9

Effects of fetal calf serum and sophorolipids in acid form on the adhesion of fibroblasts after the sowing of cells in culture wells that are not covered with collagen. Measurement of the reduction of MTT

|  | Control | SVF (%, v/v) | | Sophorolipids in acid form (mg/ml) | | |
| --- | --- | --- | --- | --- | --- | --- |
|  |  | 2 | 10 | 0.2 | 1 | 5 |
| DO/culture wells | 2.00 | 1.98 | 3.04 | 3.48 | 1.72 | 1.70 |
|  | 1.97 | 1.76 | 1.60 | 2.36 | 1.85 | 2.01 |
| mean | 1.98 | 1.87 | 2.32 | 2.92 | 1.78 | 1.85 |
| % relative to the control | 100 | 94 | 117 | 147 | 90 | 93 |

TABLE 10

Effects of fetal calf serum and sophorolipids in acid form on the adhesion of fibroblasts after the sowing of cells in culture wells that are not covered with collagen. Measurement of the reduction of MTT

|  | Control | SVF (%, v/v) | | Sophorolipids in acid form (mg/ml) | | |
| --- | --- | --- | --- | --- | --- | --- |
|  |  | 2 | 10 | 0.2 | 1 | 5 |
| DO/culture wells | 2.65 | 2.93 | 3.13 | 3.56 | 2.98 | 2.36 |
|  | 2.66 | 2.60 | 2.86 | 3.84 | 2.75 | 2.72 |

TABLE 10-continued

Effects of fetal calf serum and sophorolipids in acid form on the adhesion of fibroblasts after the sowing of cells in culture wells that are not covered with collagen. Measurement of the reduction of MTT

|  | Control | SVF (%, v/v) | | Sophorolipids in acid form (mg/ml) | | |
| --- | --- | --- | --- | --- | --- | --- |
|  |  | 2 | 10 | 0.2 | 1 | 5 |
| mean | 2.65 | 2.76 | 3.00 | 3.70 | 2.86 | 2.54 |
| % relative to the control | 100 | 104 | 113 | 140 | 108 | 96 |

EXAMPLE 6

Effect of Sophorolipids in Raw Form on the Adhesion Properties of Human Dermal Fibroblasts The experimental conditions are identical to those that are described in Example 5. The specifications of the sophorolipids in raw form are those that are described in Example 2.

The effects of the sophorolipids in raw form on the adhesion of human dermal fibroblasts to a plastic surface that may or may not be covered with collagen were evaluated. Fetal calf serum was used as a reference product.

The results show that:

a) On a hydrophobic plastic substrate, not treated for the cultivation of cells and not covered with collagen
   the sophorolipids in raw form that are tested at 0.08 and 0.4 $\mu$g/ml increased by a factor of 1.3 and 1.2, respectively, the number of cells that adhere to the hydrophobic plastic substrate. At 2 $\mu$g/ml, the adhesion of the cells to this substrate was comparable to that of the control (Table 11).

b) on an untreated culture substrate, for the cultivation of cells and covered with collagen
   The sophorolipids in raw form that are tested at 0.08 $\mu$g/ml and 0.4 $\mu$g/ml increased by a factor of 1.3 the number of cells that adhere to the hydrophobic plastic substrate. At 2 $\mu$g/ml, the adhesion of the cells to this substrate was comparable to that of the control (Table 12).

In this in vitro study, the sophorolipids in raw form increased the adhesion of the fibroblasts to the culture substrate. These results could indicate a modification by the sophorolipids in raw form of the cellular membrane or components of the latter and a modulation of the relations of dermal fibroblasts with the matrix environment in particular. These data make it possible to claim that the sophorolipids in raw form contribute to skin firmness.

TABLE 11

Effects of fetal calf serum and sophorolipids in raw form on the adhesion of fibroblasts after the sowing of cells in culture wells that are not covered with collagen. Measurement of the reduction of MTT

|  | Control | SVF (%, v/v) | | Sophorolipids in acid form (mg/ml) | | |
| --- | --- | --- | --- | --- | --- | --- |
|  |  | 2 | 10 | 0.08 | 0.4 | 2 |
| DO/culture wells | 2.00 | 1.98 | 1.60 | 2.08 | 2.50 | 2.00 |
|  | 1.97 | 1.76 | 1.55 | 2.44 | 1.91 | 1.74 |
|  | 1.51 | 1.59 | 3.04 | 2.53 | 2.20 | 1.82 |

TABLE 11-continued

Effects of fetal calf serum and sophorolipids in raw form on the adhesion of fibroblasts after the sowing of cells in culture wells that are not covered with collagen. Measurement of the reduction of MTT

|  | Control | SVF (%, v/v) 2 | SVF (%, v/v) 10 | Sophorolipids in acid form (mg/ml) 0.08 | Sophorolipids in acid form (mg/ml) 0.4 | Sophorolipids in acid form (mg/ml) 2 |
|---|---|---|---|---|---|---|
| mean ± standard deviation | 1.82 ± 0.27 | 1.78 ± 0.19 | 2.06 ± 0.84 | 2.35 ± 0.23 | 2.20 ± 0.29 | 1.85 ± 0.13 |
| % relative to the control | 100 | 98 | 113 | 129 | 121 | 102 |

TABLE 12

Effects of fetal calf serum and sophorolipids in raw form on the adhesion of fibroblasts after the sowing of cells in culture wells that are not covered with collagen. Measurement of the reduction of MTT

|  | Control | SVF (%, v/v) 2 | SVF (%, v/v) 10 | Sophorolipids in raw form (µg/ml) 0.08 | Sophorolipids in raw form (µg/ml) 0.4 | Sophorolipids in raw form (µg/ml) 2 |
|---|---|---|---|---|---|---|
| DO/culture wells | 2.62 | 2.93 | 3.13 | 3.22 | 2.64 | 3.12 |
|  | 1.95 | 2.60 | 2.69 | 2.95 | 3.10 | 3.01 |
|  | 2.65 | 2.46 | 2.86 | 3.21 | 3.59 | 1.77 |
| mean ± standard deviation | 2.40 ± 0.39 | 2.66 ± 0.24 | 2.89 ± 0.22 | 3.12 ± 0.15 | 3.11 ± 0.47 | 2.63 ± 0.74 |
| % relative to the control | 100 | 111 | 120 | 130 | 130 | 110 |

EXAMPLE 7

Cosmetic Formulations with a Sophorolipid Base

The sophorolipids in acid or raw form can be introduced into both the oil phase and the aqueous phase.

If it is desired to introduce them into the oil phase, it is necessary to dissolve them in the oil phase at 70° C., just before emulsification in the aqueous phase.

In creams, gel, and serum, the sophorolipids can be introduced at the end of production, under cold conditions.

1. Moisturizing cream with sophorolipids, emulsion of the oil in water type

| | | |
|---|---|---|
| A | Sophorolipids in raw or acid form | 0.6% |
|  | phenonip | 0.5% |
|  | perfume | 0.2% |
| B | Glycerol stearate | 4% |
|  | PEG 150 distearate | 0.5% |
|  | cetearyl alcohol | 2% |
|  | sunflower seed germ oil | 2% |
|  | cetearyl octanoate | 1% |
|  | triglycerides | 8% |
|  | dimethicone | 0.5% |
| C | water | 57.10% |
| D | glycerine | 3% |
|  | carbomer 840 | 0.3% |
|  | triethanolamine | 0.3% |
|  | water | 20% |

* Prepare phase D: add, in order, glycerine, carbomer, and water, then triethanolamine.
* Heat B and C (65° C.) separately and gradually add B into C while stirring.
* Add D, reduce the temperature to 30–35° C., then add the sophorolipids as well as the preservative and the perfume.

2. Emulsions of water/oil type

The formulas are as follows:
Oil/water cream

| | |
|---|---|
| Mineral oil | 19.00% |
| polyglyceryl-3 diisostearate | 5.00% |
| glycerine | 5.00% |
| acrylate copolymer | 3.00% |
| sophorolipids in acid form | 1% |
| sodium chloride | 0.80% |
| magnesium sulfate | 0.80% |
| phenonip | 0.50% |
| perfume | 0.20% |
| water, sufficient quantity for | 100% |

3. Makeup-removal gel

| | | |
|---|---|---|
| A | Sophorolipids | 1% |
| B | hydroxypropyl guar hydroxypropyl trimonium chloride | 0.3% |
|  | hydroxyethyl cellulose | 1% |
|  | water | 86.5% |
| C | sodium methyl cocoyl taurate | 0.4% |
|  | water, sufficient quantity for | 100% |
| D | phenonip | 0.5% |
|  | nonoxynol 10 | 0.2% |
|  | perfume | 0.10% |

* Mix phase C by heating moderately.
* Hydrate phase B and gradually add phase C to it.
* Prepare phase D, mix it with the BC preparation, and finally add the sophorolipids.
* Mix until a homogeneous gel is obtained.

4. Sophorolipid serum

| | | |
|---|---|---|
| A | Sophorolipids in raw form or acid form | 1% |
|  | phenonip | 0.5% |
| B | EDTA | 0.04% |
|  | sodium sulfite | 0.01% |
|  | sodium disulfite | 0.01% |
|  | water, sufficient quantity for | 100% |
| C | xanthan gum | 0.04% |
|  | hydroxyethyl cellulose | 0.24% |

* Prepare phase B. Hydrate C with B then add A. Mix while avoiding the formation of air bubbles.

5. Eyeliner gel with sophorolipids

| | | |
|---|---|---|
| A | Sepigel 305 (Seppic) | 5% |
|  | silicone V30 | 1% |
| B | sophorolipids in raw form | 0.6% |
|  | polysorbate 20 | 5% |
|  | cetiol HE (Henkel) | 3% |
|  | phenonip | 0.6% |
|  | perfume | 0.04% |
| C | water, sufficient quantity for | 100% |

* Prepare phases A and B separately. Add C into B while stirring. When the mixture is homogeneous, add it to phase A while stirring vigorously. Reduce stirring when the mixture becomes homogeneous. Avoid the formation of air bubbles.

I claim:

1. A method for stimulating metabolism of fibroblasts of the dermis of skin, comprising administering at least one sophorolipid to said skin.

2. The method of claim 1, wherein said sophorolipid(s) are in their raw form.

3. The method of claim 1, wherein said sophorolipid(s) are in their acid form.

4. The method of claim 2, wherein said sophorolipid(s) are in a formulation in a concentration of 30 ppm to 6% by weight to volume.

5. The method of claim 3, wherein said sophorolipid(s) are in a formulation in a concentration of 30 ppm to 6% by weight to volume.

6. The method of claim 1, wherein said sophorolipid(s) are in the form of emulsions, gels or serums.

7. A method for treating scar tissue, comprising administering to scar tissue of a patient in need of such treatment an amount of at least one sophorolipid which is effective to restructure said scar tissue.

8. The method of claim 7, wherein said sophorolipid(s) are in their raw form.

9. The method of claim 7, wherein said sophorolipid(s) are in their acid form.

10. The method of claim 8, wherein said sophorolipid is in a formulation in a concentration of 30 ppm to 6% by weight to volume.

11. The method of claim 9, wherein said sophorolipid is in a formulation in a concentration of 30 ppm to 10% by weight to volume.

12. The method of claim 7 wherein said sophorolipid(s) are in the form of emulsions, gels or serums.

13. A method for restructuring skin, comprising administering to the skin of a patient in need of such treatment a skin-restructuring effective amount of at least one sophorolipid.

14. The method of claim 13 wherein said sophorolipid(s) are in their raw form.

15. The method of claim 13 wherein said sophorolipid(s) are in their acid form.

16. The method of claim 14, wherein said sophorolipid is in a formulation in a concentration of 30 ppm to 6% by weight to volume.

17. The method of claim 13, wherein said sophorolipid is in a formulation in a concentration of 30 ppm to 10% by weight to volume.

18. The method of claim 15, wherein said sophorolipid(s) are in the form of emulsions, gels or serums.

19. A method for repairing skin, comprising administering to the skin of a patient in need of such treatment a skin-repairing effective amount of at least one sophorolipid.

20. The method of claim 19 wherein said sophorolipid(s) are in their raw form.

21. The method of claim 19 wherein said sophorolipid(s) are in their acid form.

22. The method of claim 20, wherein said sophorolipid is in a formulation in a concentration of 30 ppm to 6% by weight to volume.

23. The method of claim 21, wherein said sophorolipid is in a formulation in a concentration of 30 ppm to 10% by weight to volume.

24. The method of claim 19 wherein said sophorolipid(s) are in the form of emulsions, gels or serums.

25. The method of claim 21, wherein said sophorolipid is in a formulation in a concentration of 30 ppm to 6% by weight to volume.

26. The method of claim 22, wherein said sophorolipid is in a formulation in a concentration of 30 ppm to 10% by weight to volume.

27. A method for toning skin, comprising administering to the skin of a patient in need of such treatment a skin-toning effective amount of at least one sophorolipid.

28. The method of claim 27 wherein said sophorolipid(s) are in their raw form.

29. The method of claim 27 wherein said sophorolipid(s) are in their acid form.

30. The method of claim 27 wherein said sophorolipid(s) are in the form of emulsions, gels or serums.

31. A method of stimulating synthesis of collagen in a fibroblast, comprising administering an amount of at least one sophorolipid to said fibroblast which is effective to stimulate said synthesis.

32. A method of enhancing synthesis of collagen in a fibroblast culture in vitro, comprising administering an amount of at least one sophorolipid to said fibroblast culture which is effective to enhance collagen synthesis, wherein said fibroblast culture comprises fibroblasts which are cultivated in a monolayer in a collagen lattice, or wherein said fibroblast culture is a skin model which comprises both dermis and epidermis.

* * * * *